(12) United States Patent
Hwa et al.

(10) Patent No.: US 7,527,799 B2
(45) Date of Patent: May 5, 2009

(54) ENA MINERAL BIOACTIVE SOLUTION, MANUFACTURING METHOD THEREOF AND ITS APPLICATION FOR THE OSTEOPOROSIS PREVENTION

(76) Inventors: Sung-Yong Hwa, 101-1808 Daekyeong-Kangnam-Town, 233 Kangnam-Dong, Jinju-City, Kyeongsang-Namdo (KR); Kyu-Shik Jeong, 105-1203 Woobang-Mijin-Hites, 670 Beommul-Dong, Suseong-Gu, Daegu-City 706-767 (KR); Sun-Hee Do, 103-805 Taeseong-Mansion, Bongdeok-3Dong, Nam-Gu, Daegu-City 705-023 (KR); Won-Il Jeong, 7-108 1St Daejayeon-Apt, 153 Pa-Dong, Suseong-Gu, Daegu-City 706-070 (KR); Da-Hee Jeong, 102-1307 Hyoseong-Town-Apt, Bongdeok-2Dong, Nam-Gu, Daegu-City 705-751 (KR); Gi-Ppeum Lee, 201-208 Hakcheon-Samdo-Mirae-Town, 806-5 Hakcheon-Ri, Heunghae-Eup, Buk-Gu, Pohang Kyeongbuk (KR); Eun-Mi Cho, 227-6, Daehyeon-1Dong, Buk-Gu, Daegu-City 702-820 (KR); Hoon Ji, 3-506 Kyeongnam-Apt, Changpo-Dong, Habpo-Gu, Masan-City, Kyeongsang-Namdo 631-340 (KR)

( * ) Notice: Subject to any disclaimer, the term of this patent is extended or adjusted under 35 U.S.C. 154(b) by 213 days.

(21) Appl. No.: 11/570,962

(22) PCT Filed: Apr. 15, 2005

(86) PCT No.: PCT/KR2005/001095

§ 371 (c)(1),
(2), (4) Date: Dec. 19, 2006

(87) PCT Pub. No.: WO2006/011707

PCT Pub. Date: Feb. 2, 2006

(65) Prior Publication Data

US 2008/0274205 A1  Nov. 6, 2008

(30) Foreign Application Priority Data

Jul. 30, 2004  (KR) ..................... 10-2004-0060151

(51) Int. Cl.
*A61K 36/56* (2006.01)
*A61K 36/04* (2006.01)
(52) U.S. Cl. ................... 424/195.17; 424/547; 424/549
(58) Field of Classification Search ...................... None
See application file for complete search history.

(56) References Cited

FOREIGN PATENT DOCUMENTS

| JP | 03-086831 | 4/1991 |
|----|-----------|--------|
| JP | 04-173061 | 6/1992 |
| KR | 1019920000307 | 1/1992 |
| KR | 1019990083377 | 11/1999 |
| KR | 1020030011464 | 2/2003 |

OTHER PUBLICATIONS http://www.endocrineweb.com/osteoporosis/treatment.html—accessed Sep. 2008.*
http://www.mayoclinic.com/health/osteoporosis/DS00128/DSECTION=prevention—accessed Sep. 2008.*

* cited by examiner

*Primary Examiner*—Susan C Hoffman
(74) *Attorney, Agent, or Firm*—IPLA P.A.; James E. Bame

(57) ABSTRACT

The present invention is related to a method of manufacture of an alkaline mineral bioactive solution of which raw materials are squid bones burnt at a high temperature and crushed powder of red seaweeds and to compositions and health foods having the efficacy for the prevention of osteoporosis. The alkaline aqueous solutions having abundant minerals of the present invention may be used for bioactive solutions having the efficacy for the prevention and improvement of osseous diseases such as osteolysis and osteoporosis in mammals including human beings.

11 Claims, 11 Drawing Sheets

| FINDINGS OF SOLID ORGAN | | | | | | | | |
|---|---|---|---|---|---|---|---|---|
| STUDY : PATH200402 | | | | | | | SEX : FEMALE | |
| | 4 weeks | | | | | | | |
| | lung | heart | liver | spleen | pancreas | kidney | adrenal gl. | thyroid gl |
| V. control | 0/8[a] | 0/8 | 0/8 | 0/8 | 0/8 | 0/8 | 0/8 | 0/8 |
| 0.5% ENA | 0/8 | 0/8 | 0/8 | 0/8 | 0/8 | 0/8 | 0/8 | 0/8 |
| 5% ENA | 0/8 | 0/8 | 0/8 | 0/8 | 0/8 | 0/8 | 0/8 | 0/8 |
| 10% ENA | 0/8 | 0/8 | 0/8 | 0/8 | 0/8 | 0/8 | 0/8 | 0/8 |
| | 8 weeks | | | | | | | |
| | lung | heart | liver | spleen | pancreas | kidney | adrenal gl. | thyroid gl. |
| V. control | 0/8 | 0/8 | 0/8 | 0/8 | 0/8 | 0/8 | 0/8 | 0/8 |
| 0.5% ENA | 0/8 | 0/8 | 0/8 | 0/8 | 0/8 | 0/8 | 0/8 | 0/8 |
| 5% ENA | 0/8 | 0/8 | 0/8 | 0/8 | 0/8 | 0/8 | 0/8 | 0/8 |
| 10% ENA | 0/8 | 0/8 | 0/8 | 0/8 | 0/8 | 0/8 | 0/8 | 0/8 |
| | 12 weeks | | | | | | | |
| | lung | heart | liver | spleen | pancreas | kidney | adrenal gl. | thyroid gl. |
| V. control | 0/8 | 0/8 | 0/8 | 0/8 | 0/8 | 0/8 | 0/8 | 0/8 |
| 0.5% ENA | 0/8 | 0/8 | 0/8 | 0/8 | 0/8 | 0/8 | 0/8 | 0/8 |
| 5% ENA | 0/8 | 0/8 | 0/8 | 0/8 | 0/8 | 0/8 | 0/8 | 0/8 |
| 10% ENA | 0/8 | 0/8 | 0/8 | 0/8 | 0/8 | 0/8 | 0/8 | 0/8 |

[a] represents the number of significant/tested(1-8)

ENA MINERAL BIOACTIVE SOLUTION, MANUFACTURING METHOD THEREOF AND ITS APPLICATION FOR THE OSTEOPOROSIS PREVENTION

TECHNICAL FIELD

The present invention is related to a method of manufacture of ENA mineral A bioactive solution and bioactive solutions for the prevention and improvement of osteoporosis applying the same. In more detail, the present invention is related to mineral bioactive compositions manufactured by using squid bones and/or red seaweeds having abundant minerals as the main raw materials and to health foods using the above.

BACKGROUND ART

As the industrial society has been upgraded and professionalized, the dietary life of taking slow foods traditionally has been changed to the dietary life of taking fast foods, the supply of minerals that have been essential for modern people has been insufficient due to stress and contamination factors in the living environment, and the supply of calcium that has been required essentially for modern people has not been smooth.

Although minerals that are required by human bodies exist in human bodies in extremely small amounts, they assume important roles by helping to have cells grow and to maintain body tissues and controlling bodily activities. Particularly, as to calcium that assumes an important role in human body metabolism, it is essential for the prevention of osteoporosis, but it is difficult to supply a proper amount that is necessary for human beings and mammals, and it is problematic in that its intake is increased but the ratio of absorption is low.

Osteoporosis is a skeletal disease commonly suffered by aged, postclimacteric females, or males. In reality, its early diagnosis and prevention are not sufficient yet. Osteoporosis mainly occurs due to lack of hormones such as estrogen, growth hormone, androgenic hormone, etc., or occurs secondarily after thyroid diseases. Osteoporosis is a disease having symptoms of the decrease in osseous density as the amount of destruction of bones by osteoclasts exceeds the amount of production of bones by osteoblasts. It is progressed without special symptoms at first but fracture may occur readily even with a small amount of impact. In menopausal females, the reduction of osseous density occurs rapidly, and thereafter, the reduction of osseous density occurs slowly in both of females and males. In such osteoporosis, there are shown changes in calcium (Ca) in serum and total alkaline phosphatase and changes in the concentrations of hormones related to osteogenesis (such as estradiol, osteocalcin, etc.) and hormones related to osteolysis (such as parathyroid hormone, etc.). Also, the discharge of pyridinoline, which is a collagen cross-linking agent used as an index of osteolysis, in the urine is increased.

In the treatment of osteoporosis, estrogen has been administered as a supplementary therapy of hormones, and it has been reported that the supplementary therapy of hormones should have been initiated in the later part of perimenopause or in the early part of menopause in order to obtain the maximum effects (Stepan J. J. et al., (2003) Endocr Regul 37 (4): 225-238; Chen L. et al., (2000) 20 (4): 283-286). Also, the therapeutic agents of osteoporosis applied to contraindication of the administration of estrogen include calcium, bisphosphonate, calcitonin, raloxifene, vitamin D, etc.

In the meantime, calcitonin is a hormone produced in C-cells of thyroid gland. Its physiological actions in human bodies are not yet clear, but it is deemed that it is involved in the minute control of calcium homeostasis for a short time probably, and the effect of suppression of osteolysis is shown with pharmacological doses. Particularly, it has been reported that calcitonin has been more effective for high-turnover-rated osteoporosis. Examples of therapeutic agents having the effect of treatment of osteoporosis include 'Fosamax' and 'Evista' on the market showing their effects through the mechanism of suppressing damages to bones or slowing-down the speed of damages to bones through the action of hindering of the production and activities of osteoclasts as well as a new therapeutic agent of osteoporosis called 'Porteo' helping the formation of new bones by accelerating the production and activities of osteoblasts. Although, among new chemical drugs, ralroxifene has been a selective estrogen receptor modulator (SERM) and an ideal drug acting as an estrogen efficacy drug in the osseous cardiovascular system but as an estrogen antagonist in the breast and uterus, the toxicity of this drug shown during its metabolism has been reported recently (Hirsimaki P. et al., (2002) Breast J. 8 (2): 92-96).

SUMMARY OF THE INVENTION

It is, therefore, an object of the present invention to provide with ENA mineral A bioactive solution and the method of manufacture of such solution. It is another object of the present invention to provide with new mineral bioactive solutions which are useful for the prevention and improvement of osteoporosis. The present invention is related to the method of manufacture of ENA mineral A bioactive solution and compositions which are useful for the prevention and improvement of osteoporosis applying the above solution. In more detail, the present invention is related to an ENA mineral A bioactive solution composition manufactured by having squid bones and/or red seaweeds having abundant minerals as the main raw materials and health foods using the same.

The present invention is illustrated in more detail below:

The present invention is for the manufacture of an alkaline solution distributing natural minerals through refining laver, agar-agar, *Gracilaria verrucosa, Nemalion vermiculare, Bangia fusco-purpurea, Grateloupia filicina, Gigartina tenella,* and *Ceramium kondol* that are natural edible seaweeds, and red seaweed starch and squid bones, that are the main components.

The alkaline aqueous solution of the present invention is manufactured according to a method comprising the steps of:
washing and crushing squid bones and red seaweeds;
manufacturing inorganic minerals by burning crushed materials;
cooling the inorganic minerals to a room temperature and making them into minute powder;
ionizing the minute powder in water; and
obtaining an alkaline aqueous solution by precipitating and filtering the minute powder.

The above red seaweeds refer to 100% vegetable edible seaweeds that are red or purple vegetable groups as they contain red auxochromes besides chlorophylls. Their bodies are multicellular and thread-shaped or leaf-shaped most of the time, and they live in the ocean. Laver, agar-agar, *Gloiopeltis tenax,* etc. belong to these red seaweeds. Also, squid bones are called cuttlebones, that are dried white bones at the center parts of squids.

As to the method of manufacture of inorganic minerals using the above-described red seaweeds and squid bones in the present invention, it is preferable to wash cleanly and dry well the red seaweeds and squid bones and heat and burn them at 1,000 to 2,000° C. for 1 hour. After bacteria or impurities are burned completely and removed, there remain only minerals that are inorganic materials. These are then cooled completely to a room temperature and crushed into minute particles by using a pulverizer.

Next, the crushed minerals are dissolved into water by using burnt squid bones or red seaweeds.

In ionizing the water into which the above burnt minerals are dissolved, it is preferable to crush them at 80 to 100° C. with a water pump at a pressure of higher than 10 atmospheres for longer than 1 hour by using the difference in elevation. It is effective when the pressure of the water pump is greater than 10 k to the minimum. Thus ionized solution is precipitated and filtered. After a mineral sludge is precipitated naturally by having the ionized solution stood still for 15 to 35 hours, only a clear supernatant is filtered by using a precipitation filter in order to manufacture an alkaline mineral bioactive solution.

BRIEF DESCRIPTION OF THE DRAWINGS

A more complete appreciation of present invention, and many of the attendant advantages thereof, will be readily apparent as the same becomes better understood by reference to the following detailed description when considered in conjunction with the accompanying drawings wherein:

FIG. 16 shows the affect of the administration of mineral bioactive solutions on parenchymatous organs of animals that are subject to ovariotomy.

DESCRIPTION OF THE PREFERRED EMBODIMENTS OF THE INVENTION

Figure 1:
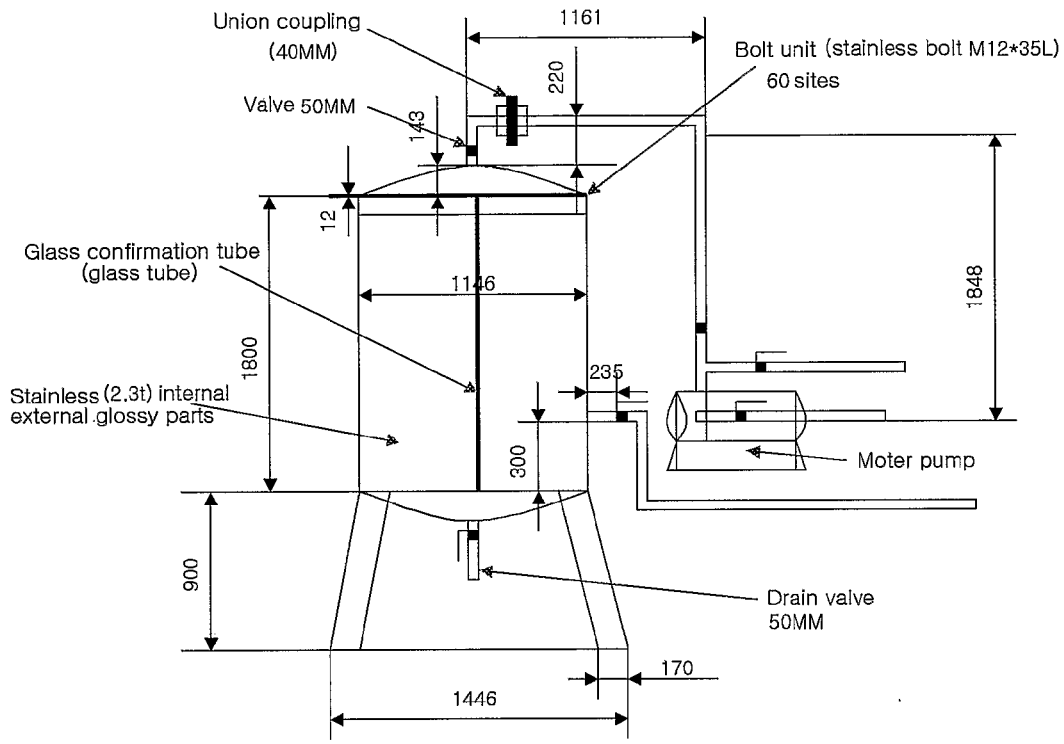
FIG. 1 shows equipment for the step of ionization of a solution.

Additional features and advantages of the present invention will be set forth in the description which follows, and in part will be apparent from the description, or may be learned by practice of the present invention. Hereinafter, % means weight % unless defined otherwise.

Preferred Embodiment 1

Manufacture of ENA Mineral A Bioactive Solution

Squid bones and red seaweeds that are washed cleanly and dried are crushed into powder and burnt at 1,100° C. for 1 hour. Burnt squid bones and seaweeds are cooled completely to a room temperature and manufactured to be minute powder by using a pulverizer. For the above red seaweeds, the same amount of each of laver, agar-agar, *Gracilaria verrucosa, Nemalion vermiculare, Bangia fusco-purpurea, Grateloupia filicina, Gigartina tenella, Ceramium kondol*, and red seaweed starch is mixed and used.

In 500 l of water, 1.5 kg of minute powder of burnt squid bones and 4 kg of minute powder of burnt red seaweeds are put, stirred, and dissolved. An ionized solution is manufactured by crushing the particles in the above solution with a water pump at a pressure of 10 atmospheres for 2 hours by using the difference in elevation. Mineral bioactive solution is manufactured by filtering the upper clear supernatant in the reactor with a precipitation filter after having the ionized solution stood still for 24 hours. The results of analysis of the components of thus manufactured mineral bioactive solution are shown in Table 1 below:

TABLE 1

Analysis of components of ENA mineral A bioactive solution
Results of tests

| Item of test | Resultant value |
|---|---|
| Iron (mg/100 g) | 0.252 |
| Calcium (mg/100 g) | 16.473 |
| Zinc (mg/100 g) | 0.100 |
| Magnesium (mg/100 g) | 0.098 |
| Sodium (mg/100 g) | 7.878 |
| Potassium (mg/100 g) | 0.953 |
| Copper (mg/100 g) | 0.012 |
| Manganese (mg/100 g) | 0.003 |
| Iodine (μg/100 g) | 1.275 |
| Phosphorus (mg/100 g) | 0.062 |
| pH | 12.85 |

As shown in the above Table 1, it is seen that the ionized solution according to the present invention is an alkaline solution with a pH of 12.85, has a high content of calcium particularly, and contains a large amount of various metal ions that are beneficial to human bodies.

Preferred Embodiment 2

Manufacture of ENA Mineral A Bioactive Solution

An ionized solution is manufactured in the same method as that in Preferred Embodiment 1 after washing cleanly and drying squid bones. And mineral bioactive solution is manufactured in the same method as that in Preferred Embodiment 1 except that 5.5 kg of minute powder of burnt squid bones is dissolved in 500 l of water. The results of analysis of the components of thus manufactured mineral bioactive solution are shown in Table 2 below:

TABLE 2

Analysis of components of ENA mineral A bioactive solution
Results of tests

| Item of test | Resultant value |
|---|---|
| Iron (mg/100 g) | 0.505 |
| Calcium (mg/100 g) | 12.529 |
| Zinc (mg/100 g) | 0.517 |
| Magnesium (mg/100 g) | 0.253 |
| Sodium (mg/100 g) | 6.777 |
| Potassium (mg/100 g) | 0.069 |
| Copper (mg/100 g) | 0.059 |
| Manganese (mg/100 g) | 0.149 |
| Iodine (μg/100 g) | Not detected |
| Crude proteins (%) | 0.168 |
| pH | 12.2 |

As shown in the above Table 2, it is seen that the ionized solution according to the present invention is an alkaline solution with a pH of 12.2, has a high content of calcium particularly, and contains a large amount of various metal ions that are beneficial to human bodies.

Preferred Embodiment 3

Animal Experiments Using the Alkaline Mineral Bioactive Solution

Animal experiments are performed by using the alkaline mineral bioactive solution manufactured in the above Preferred Embodiment 1.

As to the animals used for experiments, specific-pathogen-free (SPF) rats in the Wistar group are supplied by Orient Company and used. Five Wistar rats each are accommodated in a polycarbonate breeding box (240 W×390 L×175 H mm) equipped with an automatic hygrothermostat set at a temperature of 22±3° C., relative humidity of 50±10%, and illumination time of 12 hours (turn on at 08:00—turn off at 20:00), domesticated, and bred. As to fodder, solid fodder for experimental animals (PMI Nutrition International, 505 North 4$^{th}$ Street, Richmond, Ind. 47374, USA) is sterilized through irradiation (13.2 kGy) and taken freely. As to water, tap water is taken freely by using water bottles.

After applying 24 L of the mineral bioactive solution manufactured in Preferred Embodiment 1 to experimentally induced animal models of osteoporosis at concentrations of 0.5%, 5%, and 10% for 12 weeks as drinking water while keeping it refrigerated, experiments for the effect of prevention of osteoporosis are performed through the changes in the indexes of diagnosis of osteoporosis in serum and histopathological examination of thigh bones. General tap water is used for control experiments.

Among Wistar rats, female rats having the body weights of 200 to 230 g are selected and 24 female rats are used for each group. Rats in each individual group are accommodated in a polycarbonate breeding box. After rats are anesthetized with Rompun® (0.04 cc/100 g) and ketamine (0.14 cc/100 g), their abdomens are shaved and disinfected thoroughly with a disinfectant, and rats are subject to ovariotomy. Ovaries at both sides are removed completely by cutting about 1 cm of the medium line of abdomen by using a mess, attracting the ligamentum uteri, and exposing ovaries at both sides. Infection is prevented by thoroughly disinfecting the sites of operation after stitching each of muscle and skin, and separation of strains is performed by measuring the body weights on the next day of operation. After rats are separated in four groups, the testing material is supplied freely through drinking throughout the term of testing, and animals are sacrificed 4, 8, and 12 weeks after the administration of the testing material.

TABLE 3

Conditions for administration to each group for animal experiments

| Group | Animal I.D. | Operation | Treated with[a] |
|---|---|---|---|
| Group 1 | 1-24 | OVX | Tap water |
| Group 2 | 25-48 | OVX | 0.5% ENA[b] |
| Group 3 | 49-72 | OVX | 5% ENA[b] |
| Group 4 | 73-96 | OVX | 10% ENA[b] |

[a]Supplied freely through drinking throughout the term of testing.
[b]ENA (name of the mineral bioactive solution)

The results of animal experiments are illustrated below:

<Observation of the Changes in Body Weights of Rats>

Figure 2:
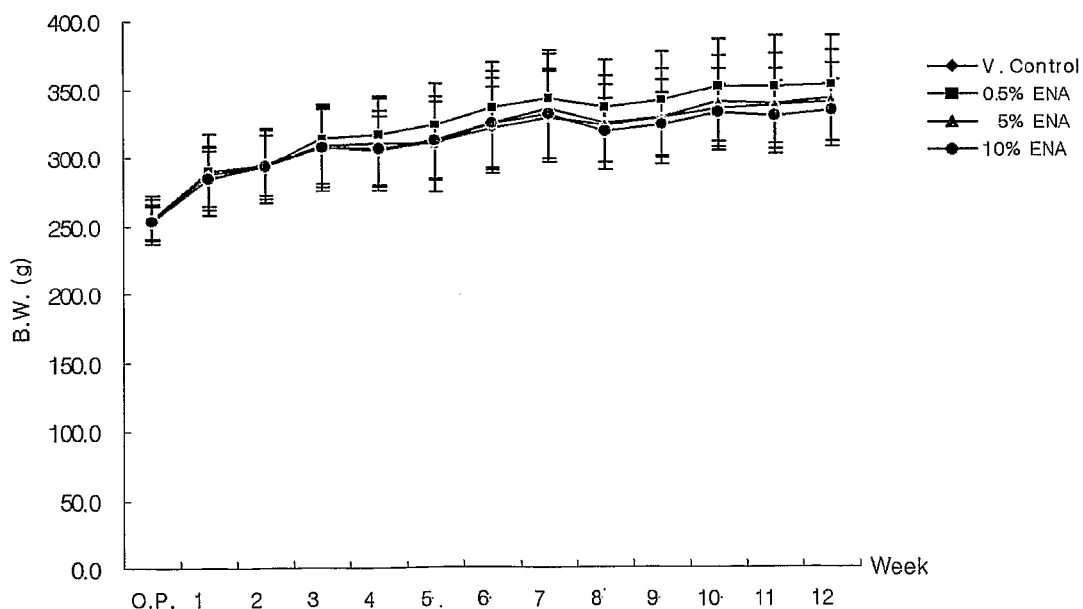
FIG. 2 shows a graph in which changes in the average body weight of animals in each group during the entire term of testing are compared.
Figure 3:
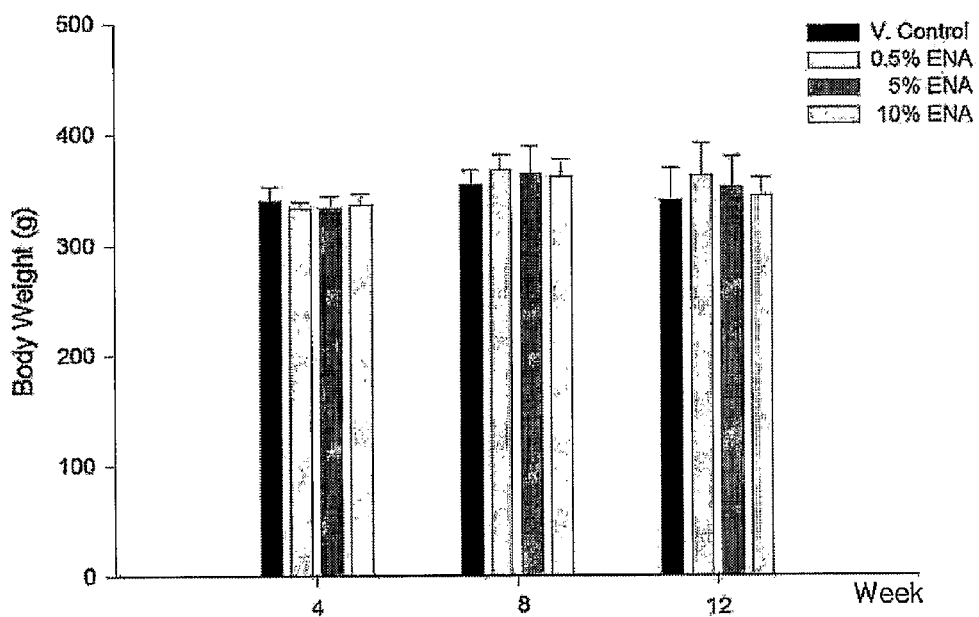
FIG. 3 is a graph showing changes in the average body weight of animals in each group measured during autopsy of animals 4, 8, and 12 weeks after the administration of the testing materials after ovariotomy.

The changes in body weights of animal models of osteoporosis induced from female rats through ovariotomy are observed by measuring body weights once a week throughout the term of testing. And general symptoms of animals are observed and shown in FIGS. 2 and 3. It is observed that body weights are increased in all testing groups after ovariotomy. But no statistically significant changes in body weights are observed in the groups to which 0.5%, 5%, and 10% mineral bioactive solutions, which are testing solutions, are administered compared to the filler control group, and no abnormal symptoms are observed throughout the term of testing in the observation of general symptoms of animals.

<Observation of the Affects on Serum Indexes>

In animal models of osteoporosis induced after performing ovariotomy experimentally to female rats, the efficacy of the testing material is verified by observing the concentrations of estradiol, osteocalcin, calcium, phosphorus, and alkaline phosphatase, that are used as serum indexes in osteoporosis, in animals that are sacrificed through period killing. After serum is separated through centrifuge of blood samples (3,000 g, for 15 minutes), estradiol and osteocalcin are measured in the radioimmunoassay method (Bayer, USA), calcium is measured in the OCPC end point method (Bayer, USA), and the concentration of phosphorus is measured in terms of spectrophotometry through the formation of phosphomolybdate complex with a commercialized kit (Bio System S.A., Buenos Aires, Argentina). The activity of serum total alkaline phosphatase is measured in terms of Coloric metric assay (Bayer, Germany). Each component is shown in FIGS. 4 through 8.

1) Calcium

Figure 4:
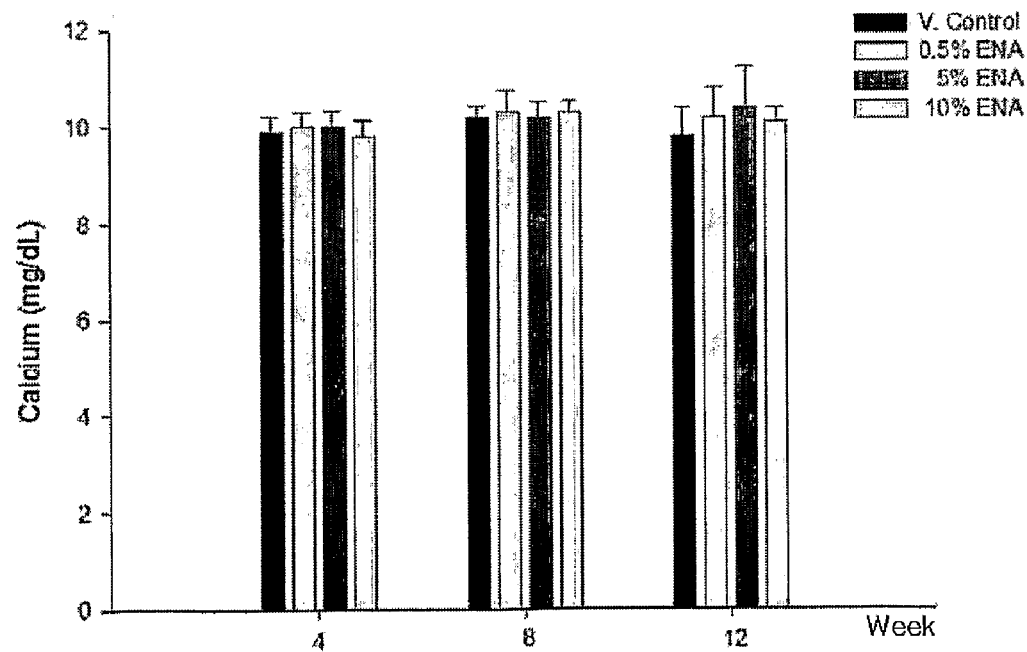
FIG. 4 shows a graph in which the effects of the mineral bioactive solutions on the changes in the concentration of calcium in serum after autopsy of animals 4, 8, and 12 weeks after the administration of the testing materials after ovariotomy.

As shown in FIG. 4, no statistically significant changes in the concentration of serum calcium are observed in the groups to which 0.5%, 5%, and 10% mineral bioactive solutions, that are testing materials, are administered throughout the term of testing compared to the filler control group. It is deemed that the administration of mineral bioactive solutions has no affect on the concentration of calcium in the blood.

2) Phosphorus

Figure 5:
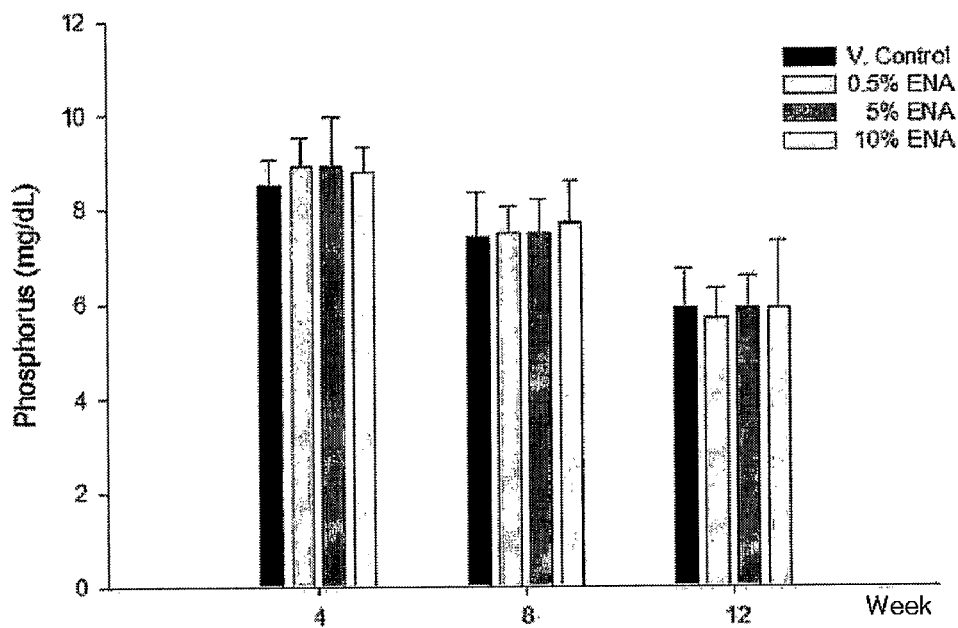
FIG. 5 shows a graph in which the effects of the mineral bioactive solutions on the changes in the concentration of phosphorus in serum after autopsy of animals 4, 8, and 12 weeks after the administration of the testing materials after ovariotomy.

As shown in FIG. 5, no statistically significant changes in the concentration of serum phosphorus are observed in the groups to which 0.5%, 5%, and 10% mineral bioactive solutions, that are testing materials, are administered throughout the term of testing compared to the filler control group. It is deemed that the administration of mineral bioactive solutions has no affect on the concentration of phosphorus in the blood.

3) Estradiol

Figure 6:
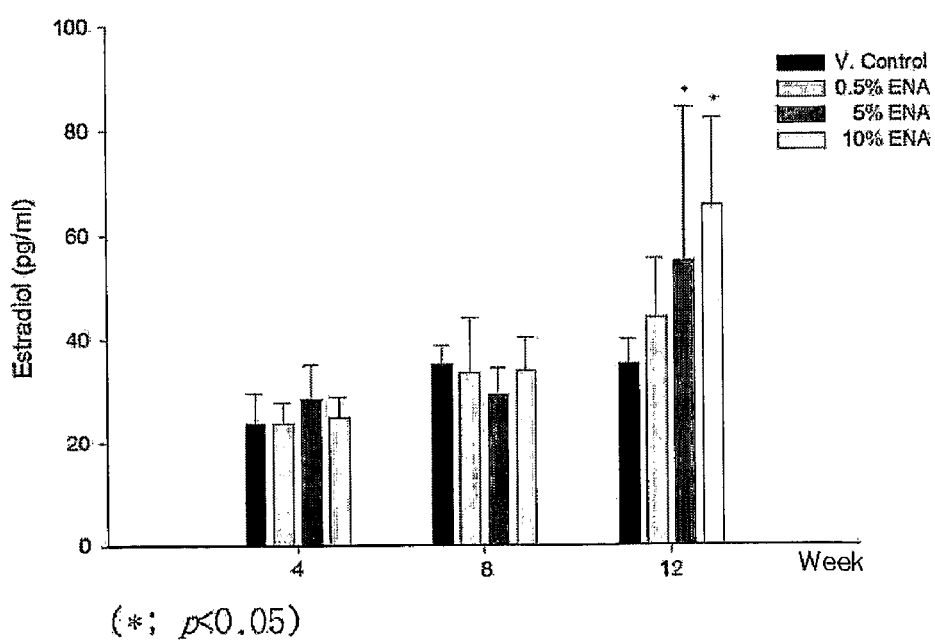
FIG. 6 shows a graph in which the effects of the mineral bioactive solutions on the changes in the concentration of estradiol in serum after autopsy of animals 4, 8, and 12 weeks after the administration of the testing materials after ovariotomy.

As seen in FIG. 6, it is observed that there is a statistically significant ($p<0.05$) increase in the concentration of serum estradiol in the groups to which 5% and 10% mineral bioactive solutions are administered 12 weeks after the administration compared to the filler control group. It is determined that such increased concentration of estradiol in the blood comes from the testing materials having natural components. And it is deemed that osteolysis may be prevented through ovariotomy in animal models of osteoporosis induced by lack of hormones.

4) Osteocalcin

Figure 7:
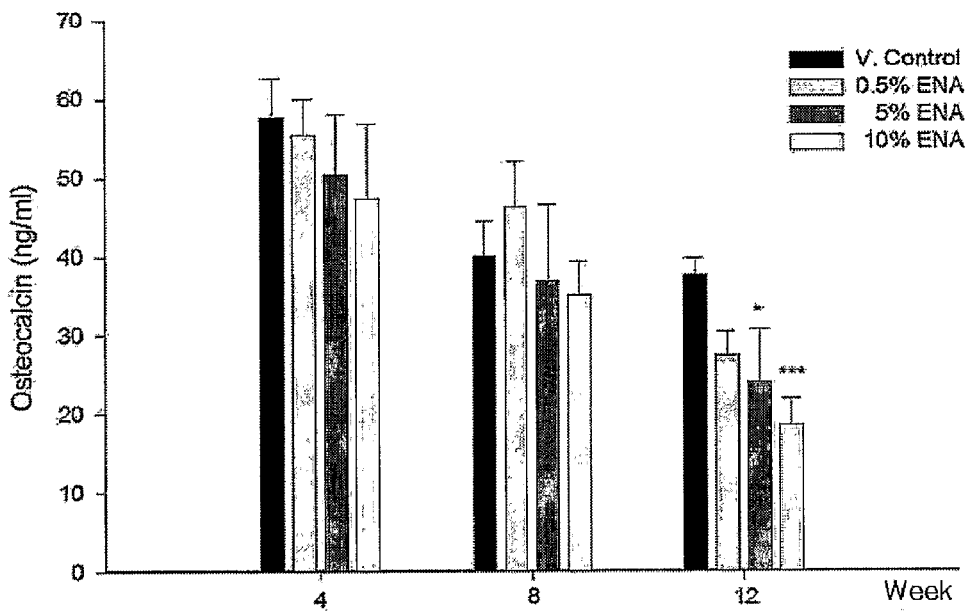
FIG. 7 shows a graph in which the effects of the mineral bioactive solutions on the changes in the concentration of osteocalcin in serum after autopsy of animals 4, 8, and 12 weeks after the administration of the testing materials after ovariotomy.

As seen in FIG. 7, it is observed that there are statistically significant ($p<0.05$ and $p<0.001$) reductions in the concentration of serum osteocalcin in the groups to which 5% and 10% mineral bioactive solutions, respectively, are administered 12 weeks after the administration compared to the filler control group. It is also observed that the concentration of serum osteocalcin tends to be low in the groups to which mineral bioactive solutions are administered 4 and 8 weeks after the administration compared to the filler control group. It is deemed that the long-term administration of the testing materials reduces osteogenesis to the original level by lowering the concentration of osteocalcin although mineral bioactive solutions do not have great affects on osteocalcin, which is an index of osteogenesis.

5) Alkaline Phosphatase

Figure 8:
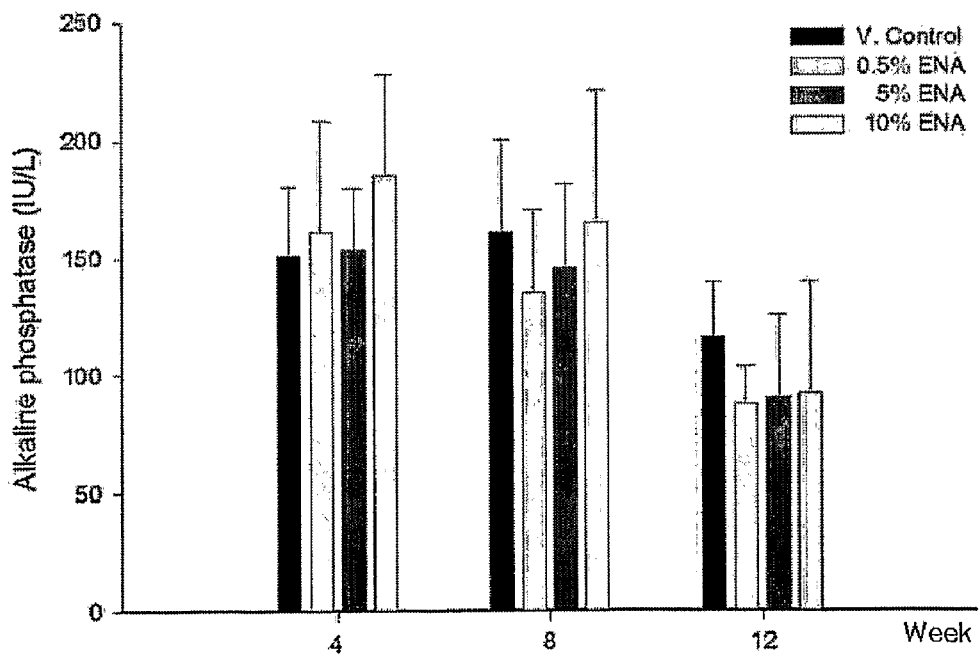
FIG. 8 shows a graph in which the effects of the mineral bioactive solutions on the changes in the concentration of alkaline phosphatase in serum after autopsy of animals 4, 8, and 12 weeks after the administration of the testing materials after ovariotomy.

As shown in FIG. 8, no statistically significant changes in the concentration of serum alkaline phosphatase are observed in the groups to which 0.5%, 5%, and 10% mineral bioactive solutions, that are testing materials, are administered throughout the term of testing compared to the filler control group.

<Observation of the Affects on Serum Pyridinoline>

Figure 9:
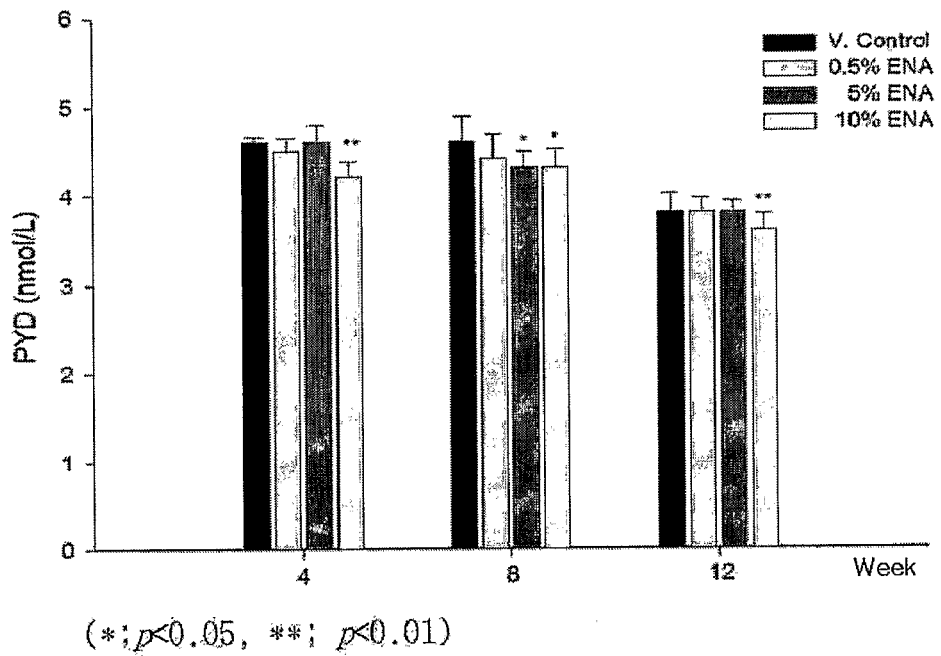
FIG. 9 shows a graph in which the effects of the mineral bioactive solutions on the changes in the concentration of pyridinoline isolated into serum during osteolysis after autopsy of animals 4, 8, and 12 weeks after the administration of the testing materials after ovariotomy.

Pyridinoline (PYD), which is a type-I collagen cross-linking molecule, is isolated into the circulated blood and urine due to the reduction of collagen of bones during osteoporosis. The progress of osteoporosis may be observed by measuring PYD, which is a bone-specific indicator. In the measurement of PYD, although the method of measurement of PYD isolated into the urine using the conventional HPLC or immunoassay has been disadvantageous in that it has had low sensitivity and specificity, it is a useful serological index for early diagnosis of osteoporosis since even 40 times lower concentration of PYD may be measured rather than PYD in serum in the urine is measured by applying enzyme-linked immunoassay (ELISA) in the present experiment. The results of measurement are shown in FIG. 9.

As a result of observation of the affects of mineral bioactive solutions on pyridinoline (PYD), which is a type-I collagen cross-linking molecule, isolated into the serum during osteolysis, as shown in Table 9, a statistically significant ($p<0.01$) reduction of the concentration of serum PYD is observed 4 and 12 weeks after the administration of the testing material in the group to which 10% testing material is administered compared to the filler control group. And a significant ($p<0.05$) reduction of the concentration of serum PYD is observed in the groups to which 5% and 10% testing materials are administered 8 weeks after the administration of the testing materials.

<Observation of the Affects on Bones and other Organs>

For the histopathological observation of thigh bones of animal models of osteoporosis induced experimentally, thigh bones are taken out from each animal sacrificed by period killing, and the area of trabecular bones, which is an index of osteoporosis, is analyzed by using an image analysis program (Visus image analysis, Foresthill Products, Foresthill, Calif., USA) through Azan staining, which is a specific staining method to collagen, in order to observe changes in collagen of thigh bones according to the progress of osteoporosis with respect to tissue specimens manufactured through the decalcification process using formic acid and tissue fixing process using 10% neutral formalin. And the number of osteoclasts, that are the cells related to osteolysis, is confirmed through hematoxylin-eosin staining.

In the meantime, for the observation of the affects of the long-term exposure to the testing materials on each organ, parenchymatous organs such as lung, heart, liver, spleen, pancreas, kidney, thyroid gland, adrenal gland, etc. are taken out along with thigh bones when sacrificing the animals, and observed through hematoxylin-eosin staining according to general tissue treatment processes through a fixing process in 10% neutral formalin. The results of observation are shown in FIGS. 10 through 16.

1) Area of Trabecular Bones

Figure 10:
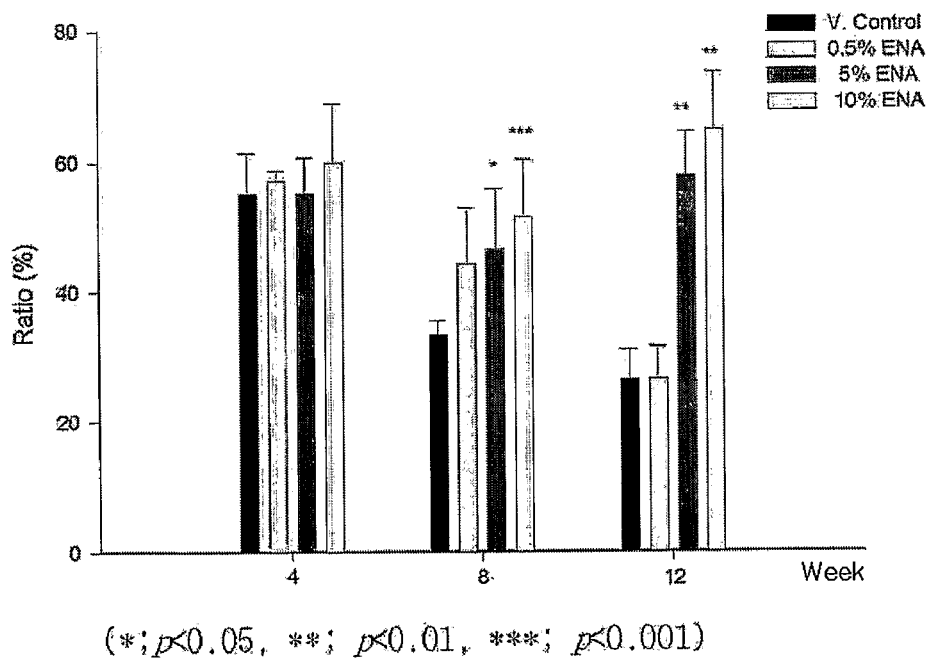
FIG. 10 shows a graph in which the effects of the mineral bioactive solutions on the changes in the area of trabecular bone tissues after autopsy of animals 4, 8, and 12 weeks after the administration of the testing materials after ovariotomy.
Figure 11:
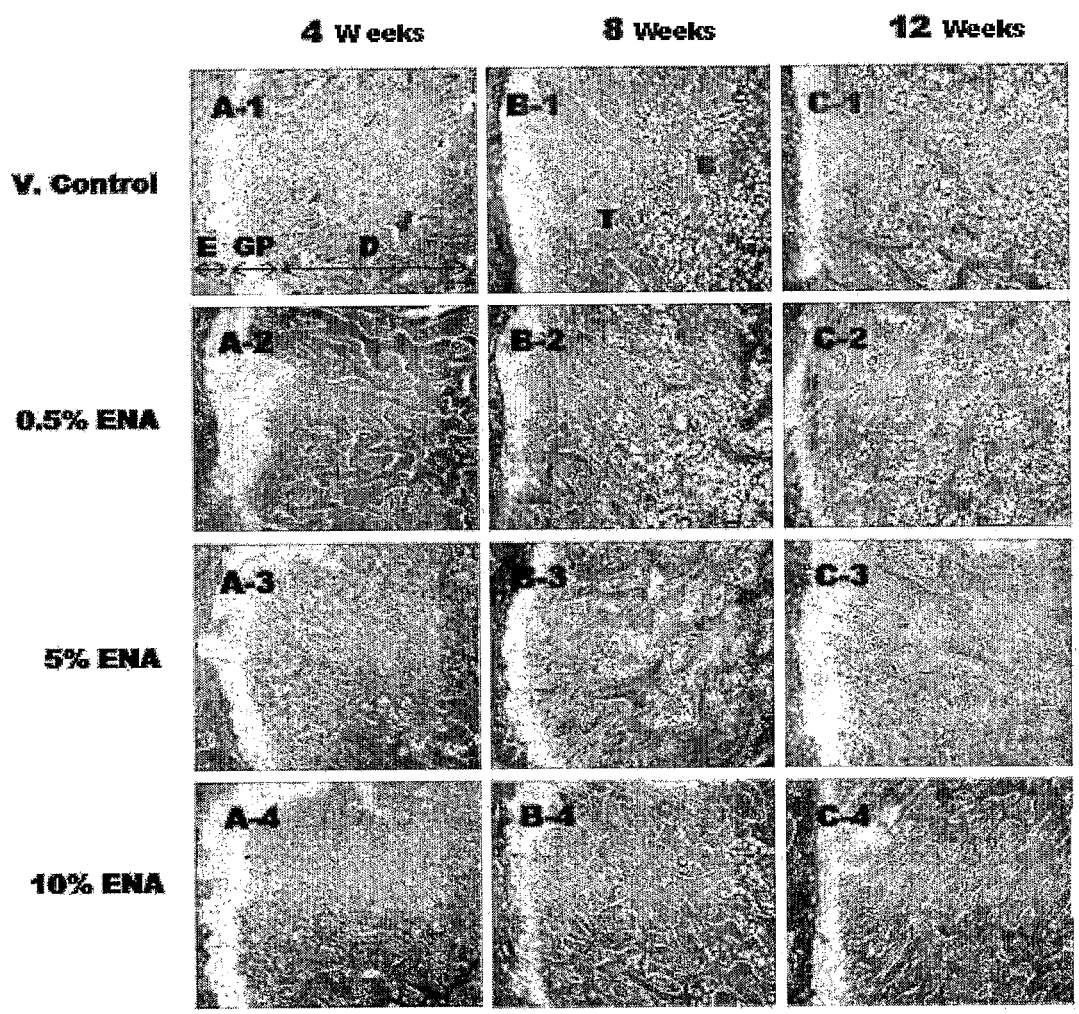
FIG. 11 shows the observation of trabecular bones, that are the indexes of osseous collagen, through Azan staining, which is a specific staining method to collagen, 4, 8, and 12 weeks after the administration of mineral bioactive solutions, which are the testing materials, after ovariotomy.
Figure 12:
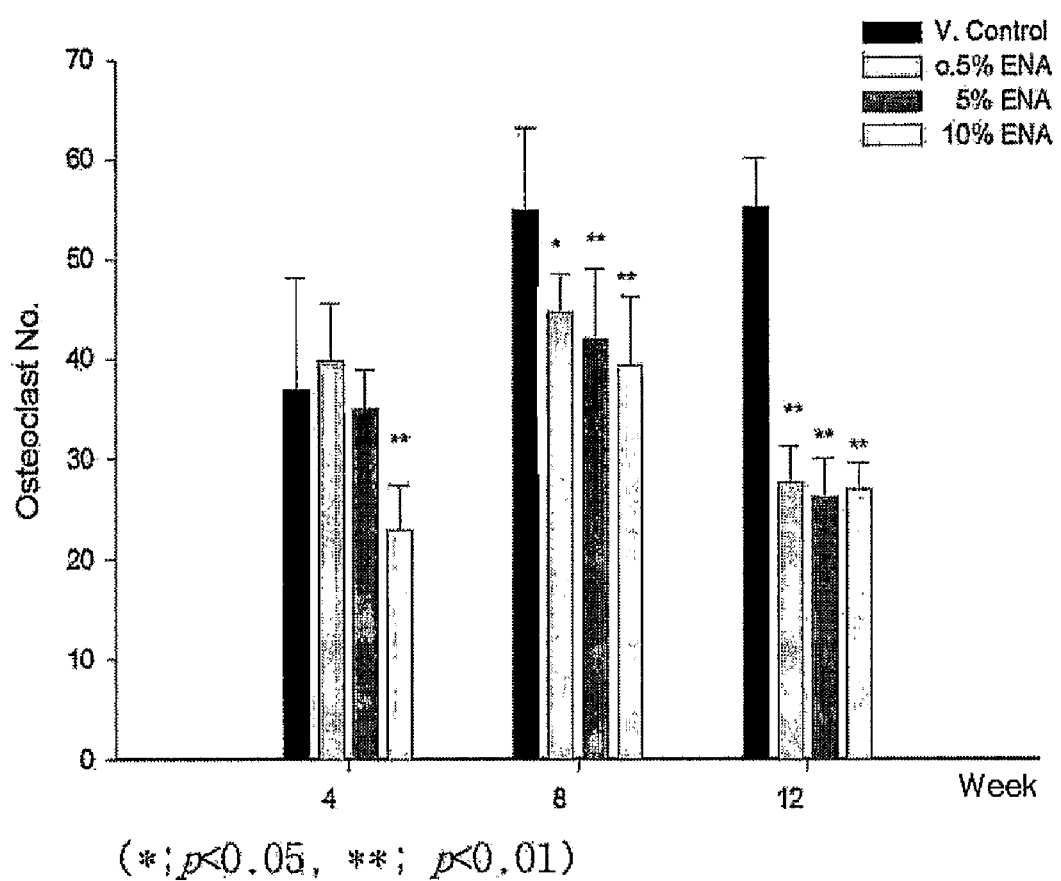
FIG. 12 shows a graph in which the effects of the mineral bioactive solutions on the changes in the number of osteoclasts increased during osteolysis after autopsy of animals 4, 8, and 12 weeks after the administration of the testing materials after ovariotomy.
Figure 13:
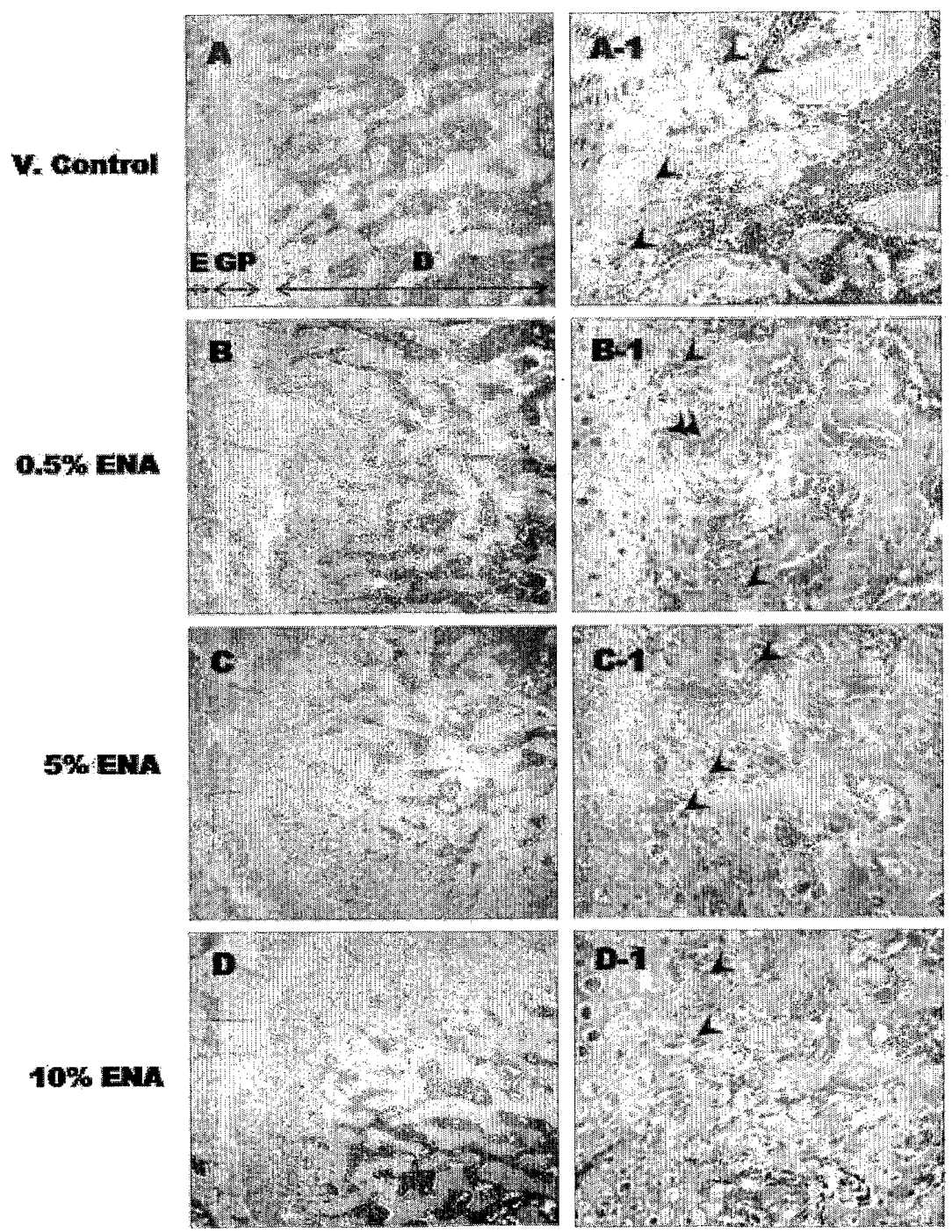
FIG. 13 shows the observation of the degree of activity of osteoclasts increased during osteolysis 4 weeks after the administration of mineral bioactive solutions, which are the testing materials, after ovariotomy.
Figure 14:
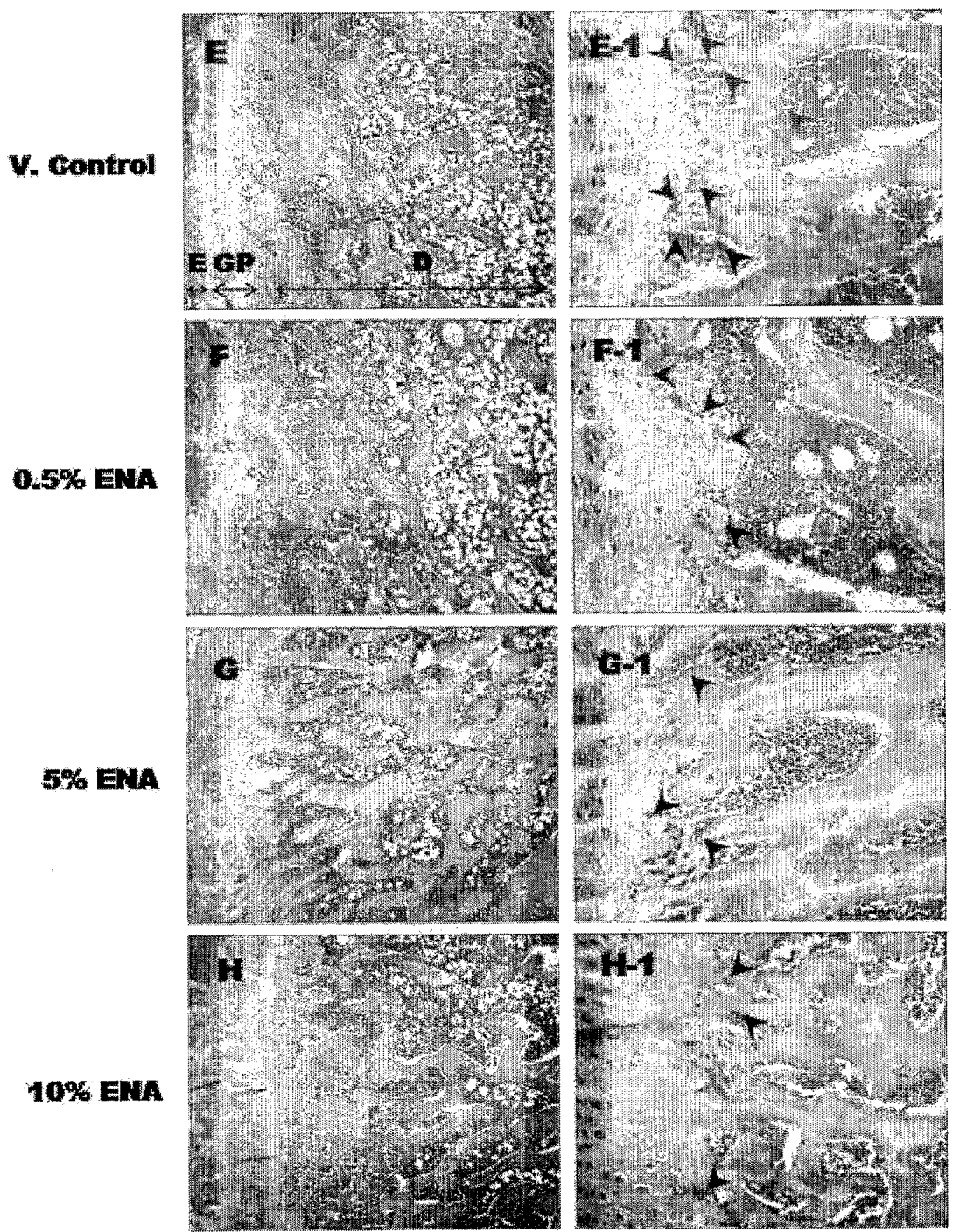
FIG. 14 shows the observation of the degree of activity of osteoclasts increased during osteolysis 8 weeks after the administration of mineral bioactive solutions, which are the testing materials, after ovariotomy.
Figure 15:
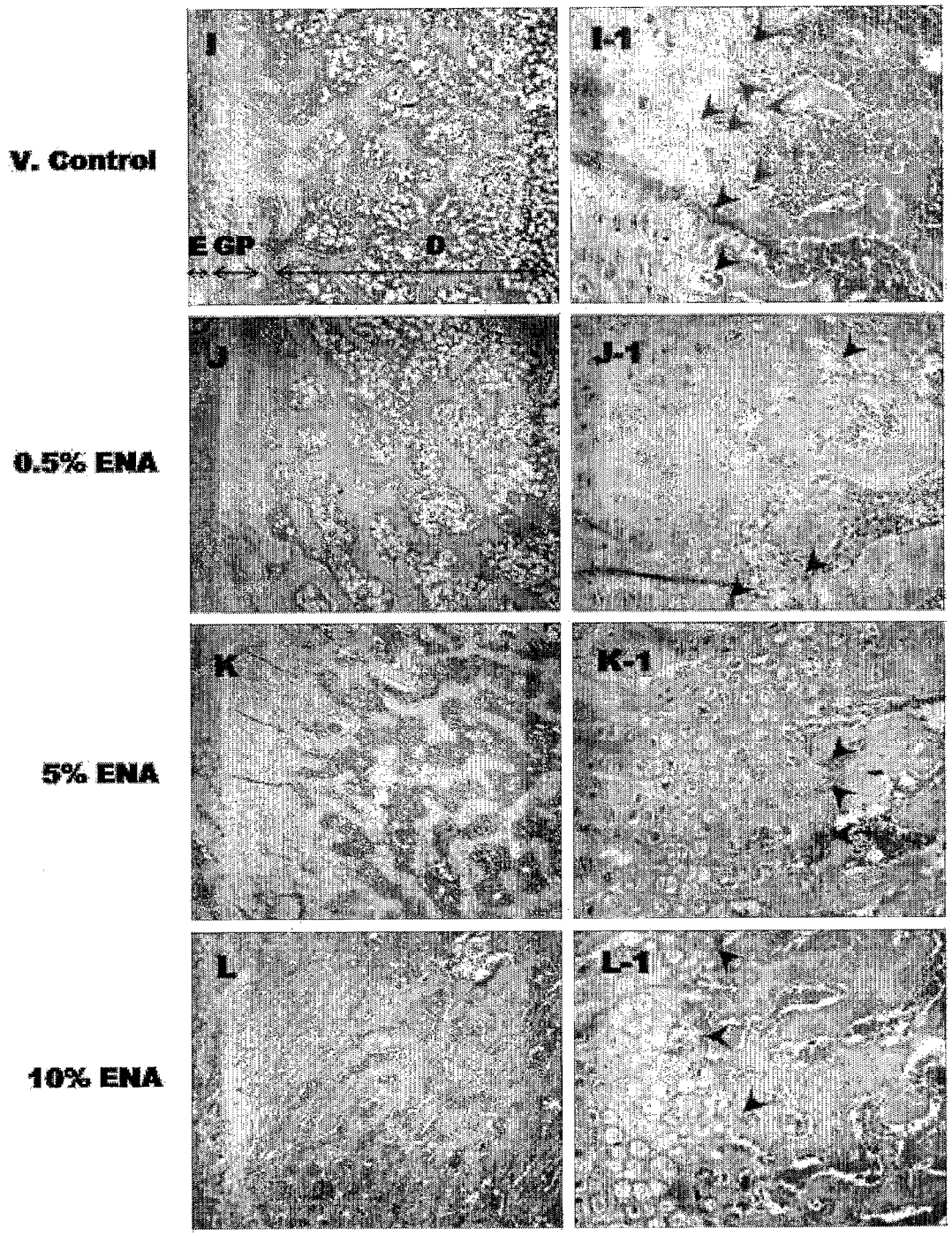
FIG. 15 shows the observation of the degree of activity of osteoclasts increased during osteolysis 12 weeks after the administration of mineral bioactive solutions, which are the testing materials, after ovariotomy.

The affects of mineral bioactive solutions, which are the testing materials, on collagen of bones after ovariotomy are reviewed through Azan staining, which is a specific staining method to collagen in tissues. As seen in FIGS. 10 and 11, it is observed that osteoporosis according to lack of hormones is progressed due to ovariotomy, and the area of trabecular bones is reduced gradually as the term of testing passes by due to decrease in the amount of bone collagen in the filler control group. Although no statistically significant changes are observed by the administration of the testing materials for 4 weeks after ovariotomy, it is observed that the area of trabecular bones, which is an index of the formation of bone collagen, tends to be somewhat high in the groups to which 0.5%, 5%, and 10% testing materials are administered compared to the filler control group. Although it is observed that bone collagen is reduced in all testing groups 8 weeks after the administration of the testing materials compared to 4 weeks after the administration, in the comparison of 8-week-administration group, statistically significant ($p<0.05$ and $p<0.001$) increases in the area of trabecular bones are observed in the groups, to which 5% and 10% testing materials, respectively, are administered, compared to the filler control group. In the meantime, in the 12-week-administration group, it is observed that the amount of bone collagen is decreased in the filler control group and the group to which 0.5% testing material is supplied compared to the 4-week- and 8-week-administration groups. And in the 12-week-administration group, as in the 8-week-administration group, a significant increase ($p<0.01$) in the area of trabecular bones is observed in both of the groups to which 5% and 10% testing materials are administered.

2) Changes in the Number of Osteoclasts

As a result of observation of the changes in the number of osteoclasts, that are the cells used for an index of osteolysis, as shown in FIGS. 12 through 15, statistically significant changes are observed throughout the term of testing. The changes in the number of osteoclasts in the diaphysis part of thigh bones are observed after the administration of mineral bioactive solution, which is the testing material, for 4 weeks after ovariotomy. A statistically significant ($p<0.01$) decrease in the number of osteoclasts is observed in the group to which 10% testing material is administered. And in the groups to which the testing materials in all concentrations are administered for 8 weeks, significant decreases in the numbers of osteoclasts are observed compared to the filler control group. In the meantime, whereas the number of osteoclasts is shown to be similarly high in the 12-week-administration group compared to the 8-week-administration group in case of the control group, it is observed that the number of osteoclasts is significantly ($p<0.01$) decreased in the groups to which the testing materials in all concentrations are administered compared to the filler control group in case of the groups to which the testing materials are administered.

3) Observation of the Affects on Parenchymatous Organs

Not only the affects of mineral bioactive solutions, which are the testing materials, but also the affects of the long-term supply of drinking water on parenchymatous organs are observed. The results show that they have no affects on lung, heart, liver, spleen, pancreas, kidney, thyroid gland, and adrenal gland. They are shown in FIG. 16.

Multiple comparison tests are performed for the materials obtained. As to the average value, Dunnett's t-test, which is a multiple comparison method, is performed in order to examine whether there is a difference among the filler control group and the administration groups if there is homogeneity in the Battlett test. If homogeneity is not recognized as a result of the Battlett test, Kruskal-Wallis's H test, which is a non-parametric method using ordered data, is performed, and the significant difference among groups is investigated by using Dunnett's test in case of $p<0.05$. Such analysis is performed by using GraphPad InStat (version 3.05, GraphPad Software Inc.), which is a statistical program. The rates of danger of verification are determined to be 5% and 1%.

INDUSTRIAL APPLICABILITY

Long-term administration of the mineral bioactive solutions according to the present invention increases the concentration of estradiol in serum but reduces the concentration of osteocalcin; prevents osteoporosis by increasing the area of trabecular bones but reducing the number of osteoclasts of thigh bones; but shows no toxicity to other organs.

While certain present preferred embodiments of the invention have been shown and described, it is to be distinctly understood that the invention is not limited thereto but may be otherwise variously embodied and practiced within the scope of the following claims.

The invention claimed is:

1. A method of manufacture of ENA mineral A bioactive solution comprising the steps of:
   washing and crushing squid bones and red seaweeds;
   manufacturing inorganic minerals by burning crushed materials;
   cooling said inorganic minerals to a room temperature and making said inorganic minerals into powder;
   ionizing said powder in water; and
   obtaining an alkaline aqueous solution by precipitating and filtering said powder.

2. The method of manufacture of ENA mineral A bioactive solution of claim 1, characterized by that said step of manufacturing said inorganic minerals is burning said crushed materials at 1,000 to 2,000° C.

3. The method of manufacture of ENA mineral A bioactive solution of claim 1, characterized by that said step of ionizing said powder in water is done at 80 to 100° C. and a pressure of 10 atmospheres or greater by using a water pump.

4. The method of manufacture of ENA mineral A bioactive solution of claim 3, characterized by that said step of ionizing said powder in water is continued for 1 hour or longer.

5. The method of manufacture of ENA mineral A bioactive solution of claim 1, characterized by that said step of precipitating is done for 15 to 35 hours.

6. The ENA mineral A bioactive solution manufactured according to claim 1.

7. The ENA mineral A bioactive solution of claim 6, characterized by that said ENA mineral A bioactive solution serves to reduce the risk of osteoporosis.

8. A method of manufacture of ENA mineral A bioactive solution comprising the steps of:
   washing and crushing squid bones and red seaweeds;
   manufacturing inorganic minerals by burning crushed materials at 1,000 to 2,000° C.;
   cooling said inorganic minerals to a room temperature and making said inorganic minerals into powder;
   ionizing said powder in 80 to 100° C. water at a pressure of 10 atmospheres or greater by using a water pump; and
   obtaining an alkaline aqueous solution by precipitating and filtering said powder.

9. The method of manufacture of ENA mineral A bioactive solution of claim 8, characterized by that said step of ionizing said powder in 80 to 100° C. water is continued for 1 hour or longer.

10. The method of manufacture of ENA mineral A bioactive solution of claim 9, characterized by that said step of precipitating is done for 15 to 35 hours.

11. The ENA mineral A bioactive solution manufactured according to claim 8, characterized by that said ENA mineral A bioactive solution serves to reduce the risk of osteoporosis.

* * * * *